(12) United States Patent
Ryu et al.

(10) Patent No.: US 10,170,078 B2
(45) Date of Patent: Jan. 1, 2019

(54) METHOD OF PROCESSING OPTICAL COHERENCE TOMOGRAPHIC IMAGE AND APPARATUS FOR PERFORMING THE METHOD

(71) Applicant: SAMSUNG ELECTRONICS CO., LTD., Suwon-si (KR)

(72) Inventors: Ji-won Ryu, Suwon-si (KR); Jae-guyn Lim, Seongnam-si (KR); Woo-young Jang, Seongnam-si (KR); Jae-duck Jang, Suwon-si (KR); Seo-Young Choi, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 964 days.

(21) Appl. No.: 14/453,984

(22) Filed: Aug. 7, 2014

(65) Prior Publication Data

US 2015/0045661 A1 Feb. 12, 2015

(30) Foreign Application Priority Data

Aug. 7, 2013 (KR) .................. 10-2013-0093798

(51) Int. Cl.
*G09G 5/02* (2006.01)
*A61B 5/00* (2006.01)

(52) U.S. Cl.
CPC ............. *G09G 5/02* (2013.01); *A61B 5/0066* (2013.01); *G09G 2340/14* (2013.01)

(58) Field of Classification Search
None
See application file for complete search history.

(56) References Cited

U.S. PATENT DOCUMENTS

| 4,789,831 A | 12/1988 | Mayo, Jr. | |
| 2009/0086046 A1* | 4/2009 | Reilly | H04N 5/2353 348/222.1 |
| 2009/0091645 A1* | 4/2009 | Trimeche | H04N 5/235 348/273 |
| 2011/0157411 A1* | 6/2011 | Hata | H04N 9/045 348/223.1 |
| 2011/0158519 A1* | 6/2011 | Zhao | G06K 9/4642 382/165 |

(Continued)

OTHER PUBLICATIONS 85276695 (US Trademark), Mar. 25, 2011, LightLab Imaging, Inc.

*Primary Examiner* — Ke Xiao
*Assistant Examiner* — Jed-Justin Imperial
(74) *Attorney, Agent, or Firm* — Sughrue Mion, PLLC

(57) ABSTRACT

Provided are a method and an apparatus for processing an optical coherence tomographic image. The method of processing an optical coherence tomographic image includes obtaining an optical coherence tomographic image by irradiating light to an object; generating a color space map based on the obtained optical coherence tomographic image; normalizing data of the obtained optical coherence tomographic image; realigning the normalized data of the optical coherence tomographic image; performing a tone mapping on the realigned data of the optical coherence tomographic image; and generating a color image by mapping the data of the optical coherence tomographic image on which the tone mapping is performed, by using the generated color space map.

18 Claims, 13 Drawing Sheets

(56) References Cited

U.S. PATENT DOCUMENTS

| | | | |
|---|---|---|---|
| 2012/0236184 A1* | 9/2012 | Jia | G06T 5/005 |
| | | | 348/241 |
| 2012/0274898 A1* | 11/2012 | Sadda | A61B 3/102 |
| | | | 351/206 |
| 2013/0083999 A1* | 4/2013 | Bhardwaj | G06Q 30/0643 |
| | | | 382/165 |
| 2013/0335438 A1* | 12/2013 | Ward | G06T 5/40 |
| | | | 345/589 |

* cited by examiner

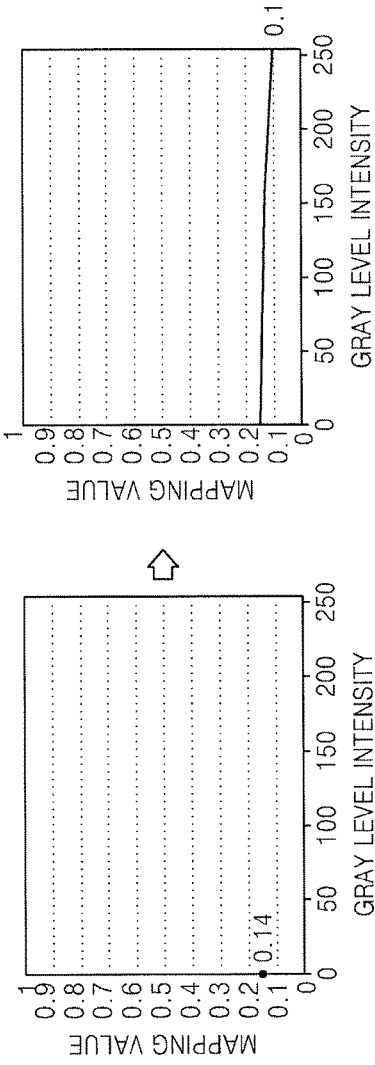
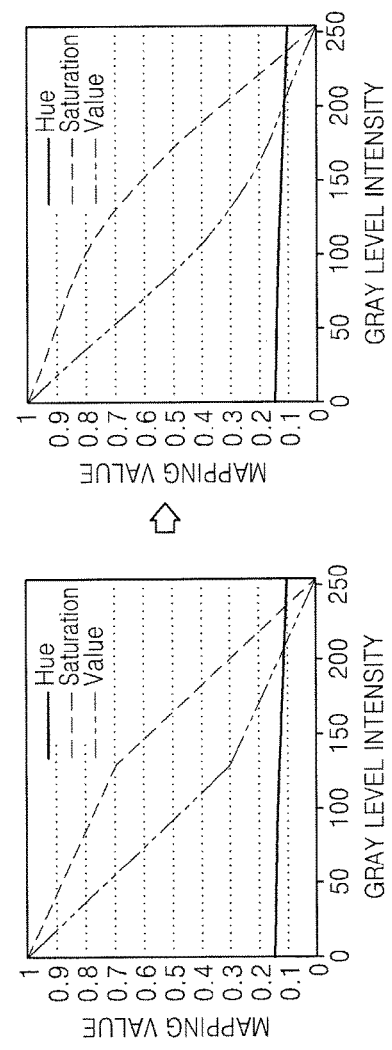

METHOD OF PROCESSING OPTICAL COHERENCE TOMOGRAPHIC IMAGE AND APPARATUS FOR PERFORMING THE METHOD

CROSS-REFERENCE TO RELATED APPLICATIONS

This application claims priority from Korean Patent Application No. 10-2013-0093798, filed on Aug. 7, 2013 in the Korean Intellectual Property Office, the disclosure of which is incorporated herein in its entirety by reference.

BACKGROUND

1. Field

Methods and apparatuses consistent with exemplary embodiments relate to processing of an optical coherence tomographic image, and more particularly, to a method of processing an image for improving discrimination of an optical coherence tomographic image.

2. Description of the Related Art

In recent years, various methods and apparatuses for observing an internal structure of an object such as human tissue or a material have been widely used in various fields. Various equipment for capturing an internal transmission image or a tomographic image, such as an X-ray system, a computerized tomography (CT) scanner, a magnetic resonance image (MRI) apparatus, or an ultrasound system, are important in a medical field because this equipment may ascertain factors, positions, and the progress of various diseases without directly incising an internal structure of a human body or a living thing. Accordingly, in such equipment, low harmfulness, a high resolution image, a reasonable price, and convenience of movement and use are recognized as important factors.

In particular, optical coherence tomography apparatuses are devices capable of imaging an internal structure of an object by using an interference phenomenon between light with which an object is irradiated and reflected, and reference light. The optical coherence tomography apparatuses have been widely used in a medical field because the optical coherence tomography apparatuses may obtain a high resolution image and are harmless to humans.

However, since an optical coherence tomographic image is expressed as a solid color image based on a gray level, it is difficult to discriminate a lesion and the like.

SUMMARY

One or more exemplary embodiments provide a method of processing an image for improving discrimination of an optical coherence tomographic image by performing pseudo color imaging through mapping using a color space map.

According to an aspect of an exemplary embodiment, there is provided a method of processing an optical coherence tomographic image including: obtaining an optical coherence tomographic image by irradiating light to an object; generating a color space map based on the obtained optical coherence tomographic image; normalizing data of the obtained optical coherence tomographic image; realigning the normalized data of the optical coherence tomographic image; performing a tone mapping on the realigned data of the optical coherence tomographic image; and generating a color image by mapping the data of the optical coherence tomographic image on which the tone mapping is performed, by using the generated color space map.

The properties of the color space map may include a hue having a linier characteristic, and a brightness and a saturation having a non-linear characteristic.

The generating the color space map may include generating a plurality of color space maps. The generating of the color image may include generating a plurality of color images by mapping the data of the optical coherence tomographic image on which the tone mapping is performed, by using the plurality of color space maps, and generating one color image by performing a weighted compounding on the generated plurality of color images.

The generating the color space map may include setting a reference hue, and setting mapping values of hue corresponding to gray level intensity values based on the reference hue.

In the setting of the reference hue, a complementary color of background hue with respect to a region indicating the object in the optical coherence tomographic image may be set as the reference hue.

In the setting of the mapping values, mapping values of hue may be set to have a linear characteristic within a predetermined range from the mapping value of the reference hue.

The generating the color space map may further include determining mapping values of brightness and saturation corresponding to two or more gray level intensity values to have a non-linear characteristic and performing an interpolation on the determined mapping values.

The normalizing the data may include adjusting the data such that gray level intensity of pixels of the optical coherence tomographic image have a value of equal to or greater than 0 and equal to or less than 1 or a value of equal to or greater than 0 and equal to or less than 255 in the case of 8 bits.

The realigning the data may include shifting the normalized data of the obtained optical coherence tomographic image such that gray level intensity having the highest frequency in the optical coherence tomographic image has a central value of all gray level intensity.

The generating the color space map may include generating a map with respect to any one color space among a hue saturation value (HSV), a hue saturation intensity (HIS), a lightness saturation hue (LCH), and a hue saturation brightness (HSB).

The performing the tone mapping may include setting an upper limit and a lower limit of a region, and performing a non-linear process on image data within the region.

The performing the non-linear process may include an enlargement of the region or a reduction of the region.

According to an aspect of another exemplary embodiment, there is provided an apparatus for processing an optical coherence tomographic image including: an image receiver configured to receive an optical coherence tomographic image; a color space map generator configured to generate a color space map based on the received optical coherence tomographic image; a normalization performer configured to normalize data of the received optical coherence tomographic image; a shifting performer configured to realign the normalized data of the optical coherence tomographic image; a tone mapping performer configured to perform a tone mapping on the realigned data of the optical coherence tomographic image; and a color space mapping performer configured to generate a color image by mapping the data of the optical coherence tomographic image on which the tone mapping is performed, by using the generated color space map.

The properties of the color space map may include a hue having a linier characteristic, and a brightness and a saturation having a non-linear characteristic.

The color space map generator may generate a plurality of color space maps. The color space mapping performer may generate a plurality of color images by mapping the data of the optical coherence tomographic image on which the tone mapping is performed, by using the plurality of color space maps, and generate one color image by performing a weighted compounding on the generated plurality of color images.

The color space map generator may set a reference hue, and set mapping values of hue corresponding to gray level intensity values based on the reference hue.

The color space map generator may set a complementary color of background hue with respect to a region indicating the object in the optical coherence tomographic image as the reference hue.

The color space map generator may set mapping values of hue to have a linear characteristic within a predetermined range from the mapping value of the reference hue.

The color space map generator may determine mapping values of brightness and saturation corresponding to two or more gray level intensity values to have a non-linear characteristic, and perform an interpolation on the determined mapping values.

The normalization performer may adjust the data such that gray level intensity of pixels of the optical coherence tomographic image have a value of equal to or greater than 0 and equal to or less than 1 or a value of equal to or greater than 0 and equal to or less than 255 in the case of 8 bits.

The shifting performer may shift the normalized data of the obtained optical coherence tomographic image such that gray level intensity having the highest frequency in the optical coherence tomographic image has a central value of all gray level intensity.

The tone mapping performer may set an upper limit and a lower limit of a region, and perform a non-linear process such as an enlargement or a reduction on image data within the region.

The tone mapping performer may perform an enlargement of the region or a reduction of the region.

According to an aspect of another exemplary embodiment, there is provided an optical coherence tomography apparatus including: a light generator configured to generate light; an optical coupler comprising a beam splitter configured to divide the light into a measurement light and a reference light, and a reference mirror configured to reflect the reference light; an optical probe configured to receive the measurement light, transmit the measurement light with which an object is irradiated, receive a response light of an irradiated measurement light which is reflected by the object, and transmit the response light to the optical coupler; a detector configured to detect an interference signal caused by the transmitted response light and the reference light; an image signal generator configured to convert the interference signal into an image signal indicating a tomographic image of the object; and an image processor configured to convert the optical coherence tomographic image into a color image by performing a pseudo color imaging on the optical coherence tomographic image through a mapping using a color space map.

The image processor may be configured to be externally connected to the optical coherence tomography apparatus.

BRIEF DESCRIPTION OF THE DRAWINGS

These and/or other aspects will become apparent and more readily appreciated from the following description of the exemplary embodiments, taken in conjunction with the accompanying drawings in which:

FIG. 4 is graphs illustrating an operation of setting a mapping value for a hue during a process of generating a color space map according to an exemplary embodiment;

FIG. 5 is graphs illustrating an operation of setting a mapping value for value and saturation during a process of generating a color space map according to an exemplary embodiment;

DETAILED DESCRIPTION OF EXEMPLARY EMBODIMENTS

Figure 1:
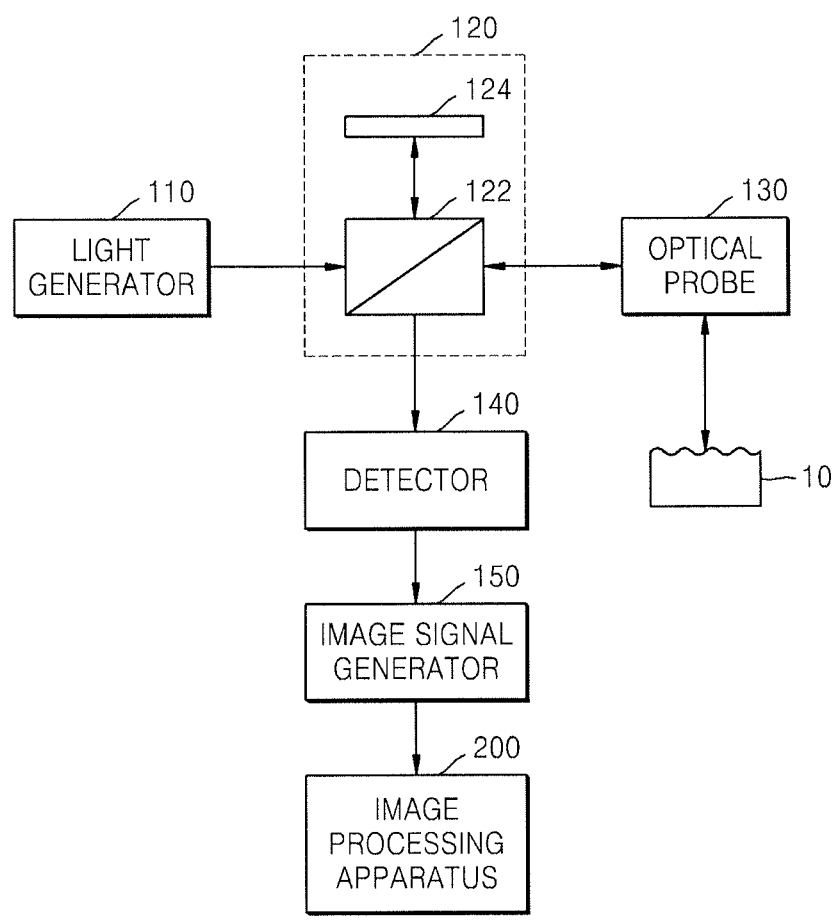
FIG. 1 is a block diagram illustrating a configuration of an optical coherence tomography apparatus including an image processing apparatus according to an exemplary embodiment.

Hereinafter, exemplary embodiments will now be described more fully with reference to the accompanying drawings. Exemplary embodiments may, however, be embodied in many different forms and should not be construed as being limited to exemplary embodiments set forth herein; rather, these exemplary embodiments are provided so that this disclosure will be thorough and complete, and will fully convey the scope of the disclosure to those skilled in the art. For example, configuring elements that are singular forms may be executed in a distributed fashion, and also, configuring elements that are distributed may be combined and then executed. In the following description, well-known functions or constructions are not described in detail since they would obscure the disclosure with unnecessary detail. Also, throughout the specification, like reference numerals in the drawings denote like elements. Expressions such as "at least one of," when preceding a list of elements, modify the entire list of elements and do not modify the individual elements of the list.

FIG. 1 is a block diagram illustrating a configuration of an optical coherence tomography apparatus including an image processing apparatus according to an exemplary embodiment.

Referring to FIG. 1, the optical coherence tomography apparatus may include a light generator 110, an optical coupler 120, an optical probe 130, a detector 140, and an image signal generator 150.

The light generator 110 generates light and transmits the light to the optical coupler 120. The optical coupler 120 may include a beam splitter 122 and a reference mirror 124. The light transmitted from the light generator 110 is divided into a measurement light and a reference light by the beam splitter 122. The measurement light is transmitted to the optical probe 130, and the reference light is transmitted to the reference mirror 124, s reflected, and returned to the beam splitter 122.

Meanwhile, an object 10 is irradiated with the measurement light transmitted to the optical probe 130, and a response light of the irradiated measurement light which is reflected by the object 10 is transmitted to the beam splitter 122 of the optical coupler 120 through the optical probe 130. The transmitted response light and the reference light reflected by the reference mirror 124 cause interference in the beam splitter 122, and the detector 140 detects an interference signal. When the interference signal detected by the detector 140 is transmitted to the image signal generator 150, the image signal generator 150 converts the interference signal into an image signal indicating a tomographic image of the object 10.

In this case, an optical coherence tomographic image that is output from the image signal generator 150 is generally a black and white image that is expressed as a gray level. Thus, it is difficult to precisely analyze the optical coherence tomographic image because a lesion has to be discriminated by using only a difference between light and shade. An image processing apparatus 200 converts the optical coherence tomographic image having a black and white image into a color image by performing pseudo color imaging on the optical coherence tomographic image to improve discrimination.

The image processing apparatus 200 may be included in the optical coherence tomography apparatus or may be externally connected to the optical coherence tomography apparatus so as to process an image output by the optical coherence tomography apparatus.

A method of processing an optical coherence tomographic image by the image processing apparatus 200 according to an exemplary embodiment will be described in detail below.

Figure 2:
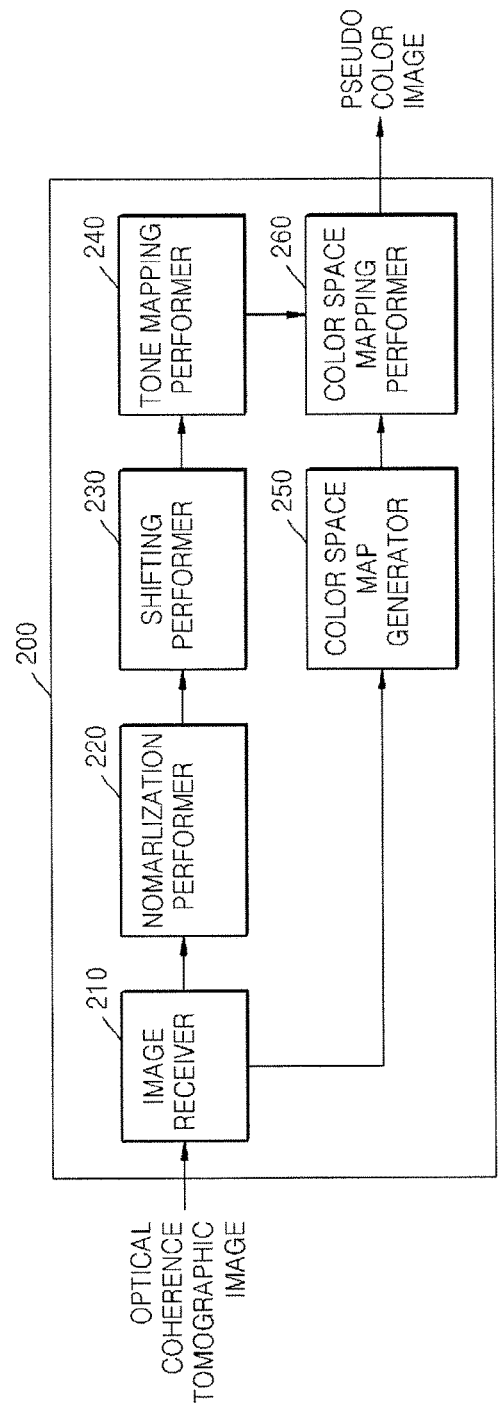
FIG. 2 is a block diagram illustrating a detailed configuration of the image processing apparatus according to an exemplary embodiment.

FIG. 2 is a block diagram illustrating a detailed configuration of an image processing apparatus according to an exemplary embodiment. Referring to FIG. 2, the image processing apparatus 200 may include an image receiver 210, a normalization performer 220, a shifting performer 230, a tone mapping performer 240, a color space map generator 250, and a color space mapping performer 260.

The image receiver 210 receives an optical coherence tomographic image that is generated and output by the image signal generator 150 of the optical coherence tomography apparatus. The received optical coherence tomographic image may be a black and white image that is expressed as a gray level, and the image receiver 210 may reverse the received optical coherence tomographic image for a pseudo color imaging process.

The normalization performer 220 receives data on the optical coherence tomographic image from the image receiver 210 and performs normalization on the data. Here, the normalization refers to a process of adjusting a numerical value of the brightness of an optical coherence tomographic image signal to be within a predetermined range.

Data on the optical coherence tomographic image includes gray level intensity regarding each pixel. For example, since the range of gray level intensity of the received image signal is excessively wide, it is difficult to perform an image processing. Accordingly, normalization is performed in such a manner that the gray level intensity has a value of equal to or greater than 0 and equal to or less than 1. In the case of 8 bits, normalization is performed in such a manner that the gray level intensity has a value of equal to or greater than 0 and equal to or less than 255.

Specifically, when the gray level intensity of the received image signal is set to I and the gray level intensity of image data on which normalization is performed is set to I', normalization is performed according to Equation 1 below.

$$I' = \frac{I(i, j) - \min(I)}{\max(I) - \min(I)} \quad (1)$$

The shifting performer 230 shifts the image data on which normalization is performed so that the image data is realigned. For example, the shifting performer 230 shifts a histogram regarding the gray level intensity of the image in order to adjust the brightness of a background signal of the optical coherence tomographic image. Specifically, the shifting performer 230 searches for a peak point of the histogram and moves the peak point to a center of the gray level intensity. Thus, in the gray level intensity of the optical coherence tomographic image, intensity having the highest frequency has a central value of all the gray levels.

Hereinafter, normalization and shifting of image data will be described in detail with reference to FIG. 7.

Figure 7:
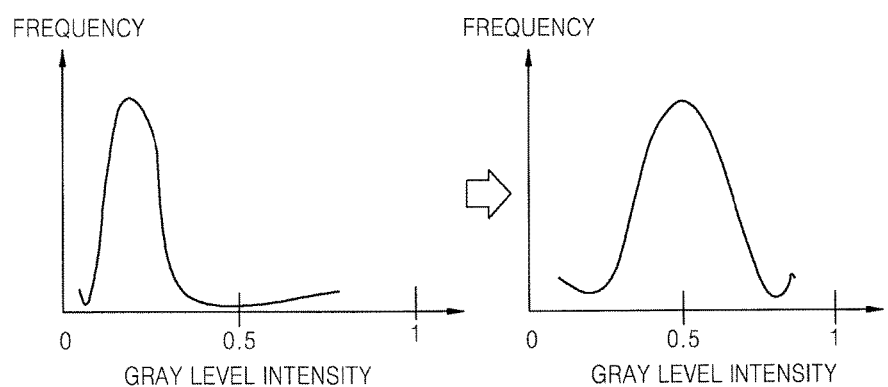
FIG. 7 is graphs illustrating a process of normalizing and shifting data of an optical coherence tomographic image according to an exemplary embodiment.

FIG. 7 is graphs illustrating a process of normalizing and shifting data on an optical coherence tomographic image according to an exemplary embodiment. A left histogram of FIG. 7 represents optical coherence tomographic image data on which normalization is performed, and a right histogram represents data on which both normalization and shifting are performed. In the histograms, a horizontal axis represents gray level intensity, and a vertical axis represents the frequency of a pixel.

Referring to the left histogram of FIG. 7, as a result of the normalization, the image data has gray level intensity from about 0 to about 1. At this time, since the gray level intensity corresponding to the peak point of the histogram is less than 0.5, the whole brightness of the image is low. If the histogram is shifted to the right so that the peak point of the histogram corresponds to 0.5 which is a central value of all the gray levels, the left histogram is changed into the right histogram of FIG. 7, and the whole brightness of the image increases. In this manner, the image is adjusted to have an appropriate brightness by realigning the image data through shifting, and thus discrimination may be increased.

Meanwhile, contrary to the example illustrated in FIG. 7, if the peak point of the histogram is within a gray level intensity range between 0.5 and 1, the histogram may be shifted to the left so that the peak point of the histogram corresponds to the gray level intensity of 0.5.

Referring back to FIG. 2, an operation of the tone mapping performer 240 will be described. After normalization and shifting are performed on optical coherence tomographic image data, a tone mapping is performed thereon. An effect of contrasting an image signal with respect to an object such as human tissue with a background may be increased by performing the tone mapping.

A specific method of performing the tone mapping is as follows. In the histogram of image data, a low range portion and a high range portion of gray level intensity are treated as a noise or a saturated signal, and the remaining practical signal portions may be stretched so as to increase the precision of an actual interest region in the image. In addition, at this time, since any signal is not removed, structure constancy is maintained, and only the precision regarding the interest region in the image may be increased.

Figure 8:
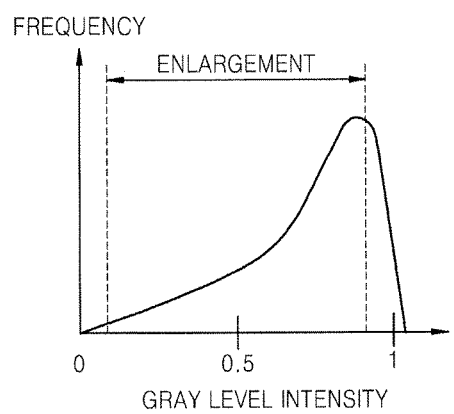
FIG. 8 is a graph illustrating a result of tone mapping performed on image data according to an exemplary embodiment.

FIG. 8 is a graph illustrating a result of tone mapping performed on image data according to the exemplary embodiment. Referring to FIG. 8, in a histogram having a peak point at gray level intensity of 0.5, a region thereof is set in such a manner that points having gray level intensity of 0.20 and 0.55 are a lower limit and an upper limit, respectively. When the histogram within the set region is enlarged so as to have the gray level intensity 0.10 and 0.90 as a lower limit and an upper limit respectively, the histogram as illustrated in FIG. 8 may be obtained.

That is, if a region having gray level intensity corresponding to an actual interest region is set and the set region is enlarged, a difference in brightness in the actual interest region may be shown more minutely in the image.

The image processing apparatus 200 may further include a median filter (not shown) for removing noise of image data so as to perform noise removal filtering after performing the tone mapping.

After normalization, shifting, and tone mapping are performed on the optical coherence tomographic image, a color space mapping is performed thereon so as to generate a pseudo color image. The color space map generator 250 generates a color space map that is used for mapping, based on the received optical coherence tomographic image. The color space map generator 250 may generate a map for various color spaces such as a hue saturation value (HSV), a hue saturation intensity (HSI), a lightness chroma hue (LCH), and a hue saturation brightness (HSB).

Figure 3:
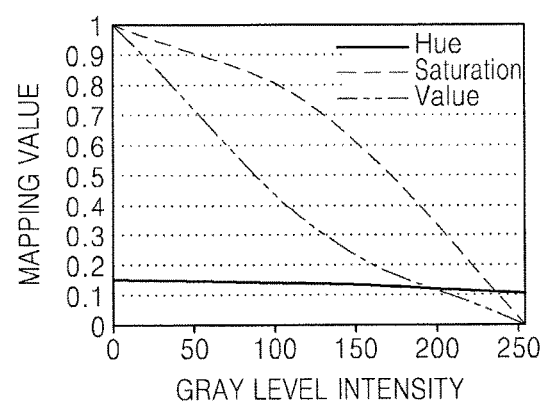
FIG. 3 is a graph illustrating a color space map that is generated according to an exemplary embodiment.

FIG. 3 is a graph illustrating an HSV map that is generated according to the exemplary embodiment. In the HSV map, a horizontal axis represents gray level intensity, and a vertical axis represents a mapping value. The HSV map defines mapping values corresponding to various gray level intensity values with respect to properties of hue, saturation, and value. Here, the HSV map has a linear characteristic with respect to hue, but has a non-linear characteristic with respect to saturation and value.

Since the HSV map has a non-linear characteristic with respect to saturation and value, there is an effect that discrimination of an interest region in the optical coherence tomographic image may be improved. This is, because an interest region is located around a central value of all gray level intensity values by the normalization and shifting performed on the image, an image after the mapping has a larger difference between light and shade than that of an original image by increasing a slope of a mapping value for the gray level intensity around the interest region.

Meanwhile, when the HSV map is generated, a reference hue is set, and a mapping value is defined so as to have a linear characteristic within a predetermined range from a mapping value of the reference hue. The reference hue is set to be complementary to background hue other than an interest region showing an object in the original optical coherence tomographic image, thereby improving discrimination.

Accordingly, if the reference hue of the interest region is set to be complementary to background hue, the interest region may be clearly discriminated from a background, and discrimination may be improved through mapping having a non-linear characteristic with respect to value and saturation within the interest region.

Hereinafter, a detailed process of generating an HSV map will be described with reference to FIGS. 4 to 6D.

FIG. 4 is graphs illustrating an operation of setting a mapping value for hue during a process of generating the HSV map according to the exemplary embodiment. In a left graph of FIG. 4, a mapping value of 0.14 is set as reference hue to correspond to gray level intensity of 0. A background of an optical coherence tomographic image is generally black, and yellow which is complementary to black is set as the reference hue. In a right graph of FIG. 4, a linear mapping with respect to hue is performed so that a mapping value of 0.1 corresponds to gray level intensity of 255. While a range in which a mapping value of hue is present may be freely set as required, the range may be set not to be excessively wide so that a complementary color with respect to a background of the optical coherence tomographic image may be maintained.

FIG. 5 is graphs illustrating operations of setting a mapping value for value and saturation during a process of generating an HSV map according to the exemplary embodiment. In a left graph of FIG. 5, mapping values corresponding to gray level intensity values of 0, 127, and 255 are set, and the set mapping values are connected linearly. At this time, the mapping values are set not to be present on one straight line to have a non-linear characteristic. In addition, the mapping values are set such that an interest region of the optical coherence tomographic image is clearly shown.

For example, when a mapping graph for value and saturation is bent as illustrated in the left graph of FIG. 5, an image that is mapped using an HSV map includes a large amount of speckle noise. Thus, in order to prevent an occurrence of the speckle noise, an interpolation may be performed on the HSV map of the left graph of FIG. 5. As a result, the HSV map is changed to an HSV map as illustrated in the right graph of FIG. 5. At this time, for example, a cubic spline interpolation may be performed.

That is, with respect to value and saturation, two or more mapping values are set as reference points, and the interpolation is performed, thereby a map having a non-linear characteristic may be obtained.

Figure 10:
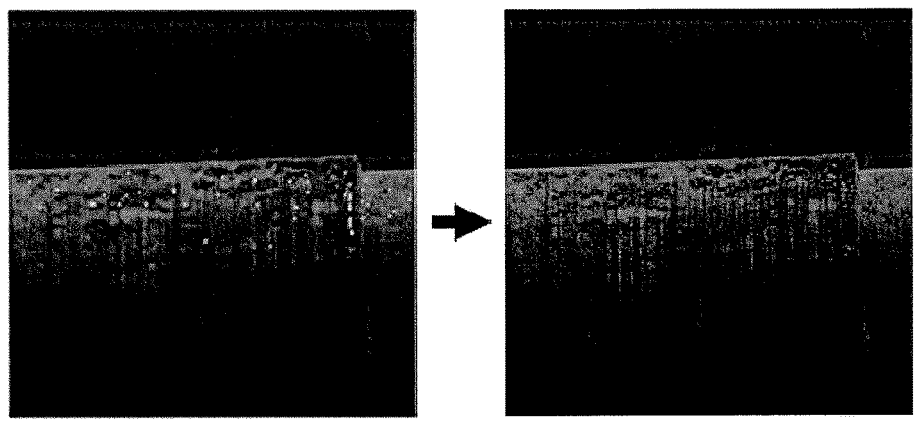
FIG. 10 illustrates an image on which interpolation has not been performed and an image on which interpolation has been performed in a method of processing an optical coherence tomographic image according to an exemplary embodiment.

In order to compare effects obtained by performing interpolation, FIG. 10 illustrates an image (left image) on which mapping is performed by using an HSV map on which interpolation is not performed, and an image (right image) on which mapping is performed using an HSV map on which interpolation is performed. Referring to FIG. 10, in the right image on which mapping is performed using an HSV map on which interpolation is performed, speckle noise is remarkably reduced as compared with the left image.

FIGS. 6A to 6D are graphs illustrating various HSV maps according to exemplary embodiments.

Figure 6A:
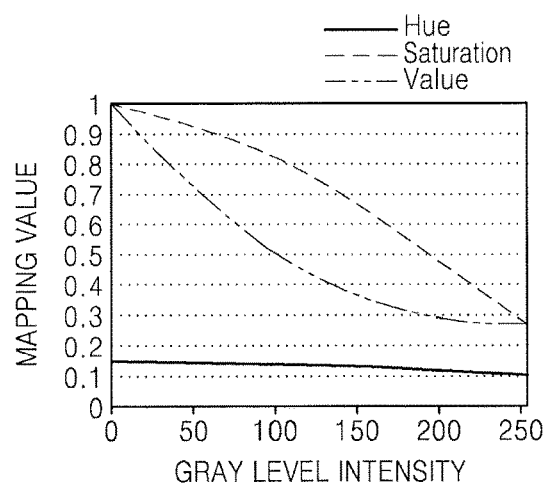
FIGS. 6A to 6D are graphs illustrating various color space maps according to exemplary embodiments.

Referring to FIG. 6A, a mapping value corresponding to gray level intensity of 255 is approximately 0.28. For example, a minimum value of the mapping value with respect to value and saturation may be greater than 0, and a maximum value of the mapping value with respect to value and saturation may be less than 1.

Figure 6B:
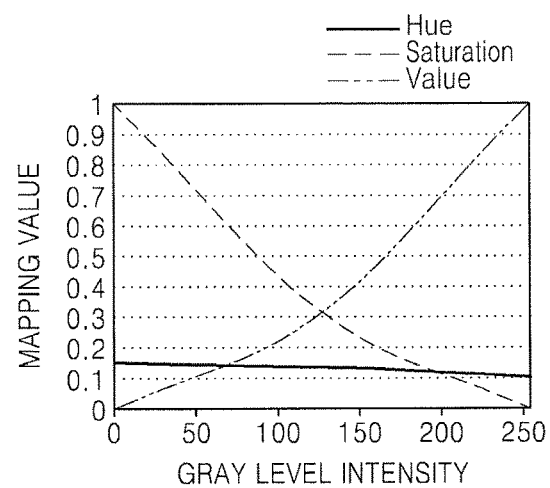
Figure 6C:
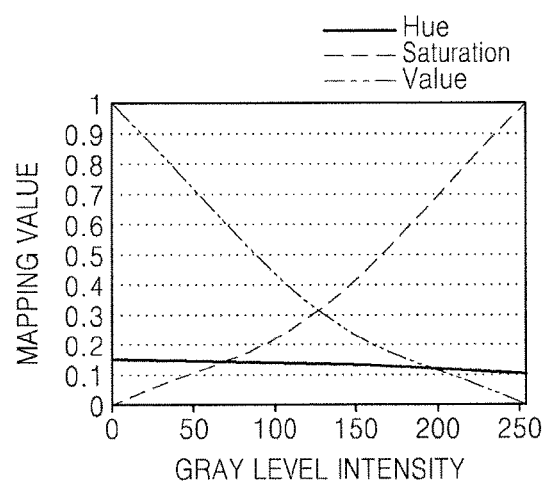

Referring to FIGS. 6B and 6C, a mapping graph with respect to value and saturation may be set in various directions while maintaining its non-linear characteristic.

Figure 6D:
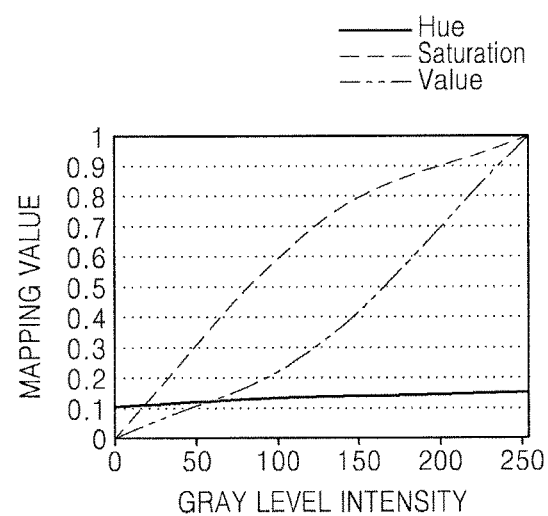

Referring to FIG. 6D, a direction of a slope of the mapping graph with respect to value and saturation may be set to be opposite to that in the graph of FIG. 3.

Besides, an HSV map having a non-linear mapping characteristic with respect to value and saturation may be configured in various ways.

The color space mapping performer 260 may output a pseudo color image by mapping the image data received from the tone mapping performer 240 by using the HSV map that is generated by the color space map generator 250. Specifically, the color space mapping performer 260 may obtain a color image by converting the gray level intensity of each pixel of the optical coherence tomographic image into corresponding color by using a color space map. At this time, an image on which mapping is performed using the HSV map may be converted into an RGB (red, green, blue) domain so that a user may discriminate the image.

Figure 9:
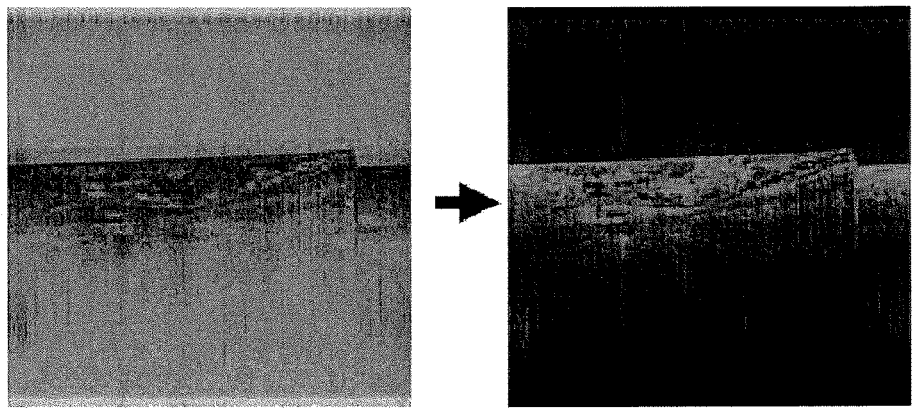
FIG. 9 is images illustrating an optical coherence tomographic image that has not been processed and an optical coherence tomographic image that has been processed according to an exemplary embodiment.

FIG. 9 illustrates an optical coherence tomographic image that has not been processed and an optical coherence tomographic image that has been processed according to an exemplary embodiment. A left image of FIG. 9 is an image of an original image that is reversed, and a right image of FIG. 9 is a pseudo color image that is obtained by performing HSV mapping on the reversed image.

The color space map generator 250 generates a plurality of different color space maps, and the color space mapping performer 260 may perform image data mapping on each of the plurality of color space maps and synthesize a plurality of color images that are obtained through the image data mapping to obtain one color image.

In this manner, mapping is performed using the plurality of color space maps, and images are synthesized, thereby improving discrimination. For example, an image that is mapped using a color space map for improving contrast in an axial direction is synthesized with an image that is mapped using a color space map for improving contrast in a transverse direction, and both the contrast in the axial direction and the transverse direction may be improved.

In addition, if images on which mapping is performed are synthesized using a plurality of color space maps, such as color space map for clearly showing a surface structure, a color space map for clearly showing a lower portion, and a color space map for clearly showing the entirety, a color image with a significantly improved discrimination may be obtained.

At this time, the images that are generated using the plurality of color space maps may be synthesized using a weighted compounding method. For example, when three color images CI1, CI2, and CI3 are generated using three color space maps, a color image CI that is synthesized according to Equation 2 below may be obtained using a, b, and c that satisfy a relation of a+b+c=1.

$$aCI1+bCI2+aCI3=CI \qquad (2)$$

In addition, when a plurality of color images are generated using the plurality of color space maps, levels of saturation and value are set to be different from each other in the plurality of color images, but hue is constantly set in order to maintain color constancy.

Figure 11:
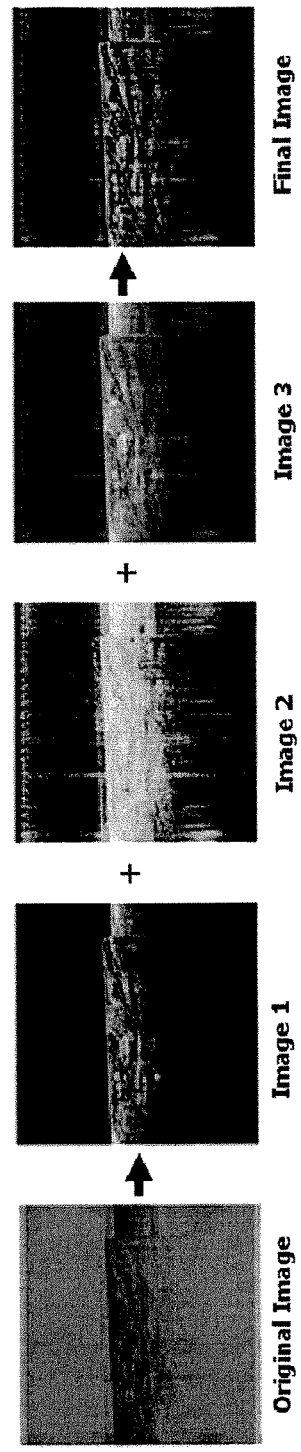
FIG. 11 illustrates images that are mapped and synthesized using a plurality of different color space maps in a method of processing an optical coherence tomographic image according to an exemplary embodiment.

FIG. 11 illustrates an original image, color images of Image 1, Image 2, and Image 3 that are obtained by mapping the original image by using three different HSV maps, and a final image that is obtained by synthesizing the three color images.

The first image (Image 1) is an image that is mapped using the HSV map in which slopes of saturation and value are set to be sharp so that a structure of a surface line of tissue is clearly shown, the second image (Image 2) is an image that is mapped using the HSV map to which a slope function is applied so that a resolution in the axial direction is improved, and the third image (Image 3) is an image that is mapped so as to improve the whole contrast.

Then, a weighted compounding is applied to the three images (Image 1, Image 2, and Image 3), and the final image may be obtained.

Figure 12:
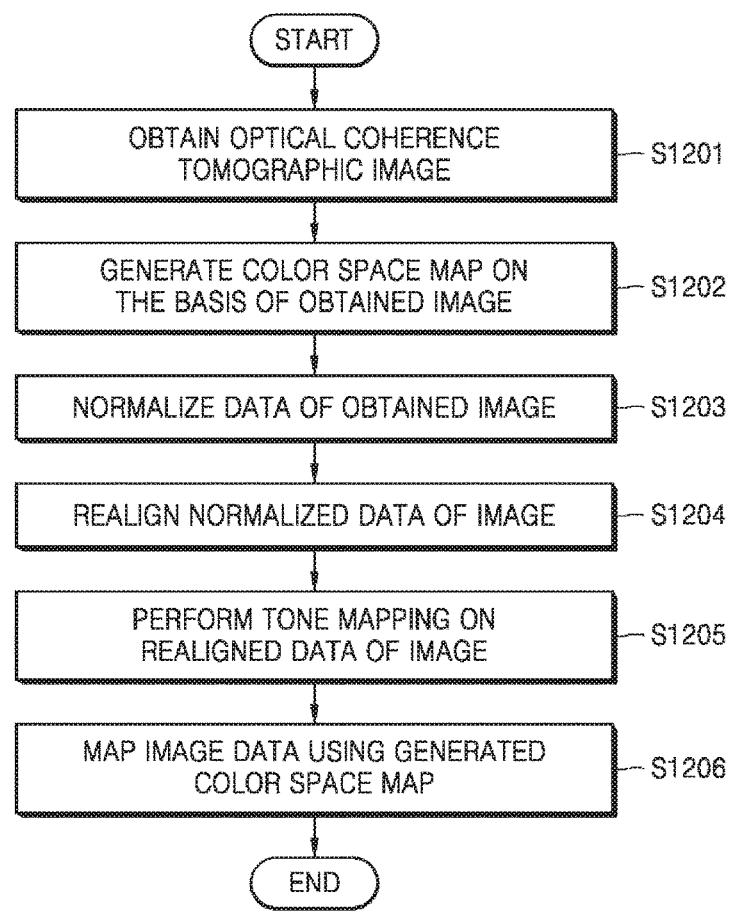
FIGS. 12 to 15 are flowcharts illustrating a method of processing an optical coherence tomographic image according to exemplary embodiments.

FIG. 12 is a flowchart illustrating operations of performing a pseudo color imaging on an optical coherence tomographic image according to the exemplary embodiment.

Referring to FIG. 12, the optical coherence tomographic image is obtained in operation S1201. At this time, the obtained optical coherence tomographic image is a black and white image that is expressed as a gray level. The obtained optical coherence tomographic image may be reversed for the subsequent process.

In operation S1202, a color space map is generated based on the obtained optical coherence tomographic image. At the time, a complementary color of background color of the optical coherence tomographic image is set as a reference hue. Mapping value for hue is set to have a linear characteristic, and mapping values with respect to saturation and value are set to have a non-linear characteristic so that an interest region of the optical coherence tomographic image is clearly shown.

Data of the obtained optical coherence tomographic image is normalized in operation S1203, the normalized data of the optical coherence tomographic image is realigned in operation S1204, and tone mapping is performed on the realigned data of the optical coherence tomographic image to improve contrast of the data of the optical coherence tomographic image in operation S1205.

In operation S1206, the image data is mapped using the generated color space map, and thus a pseudo color image is generated. In the generated pseudo color image, an interest region indicating tissue and the like is expressed as a complementary color of a background, and the interest region has a great difference between value and saturation, and thus the pseudo color image has an improved discrimination as compared with the original image.

Figure 13:
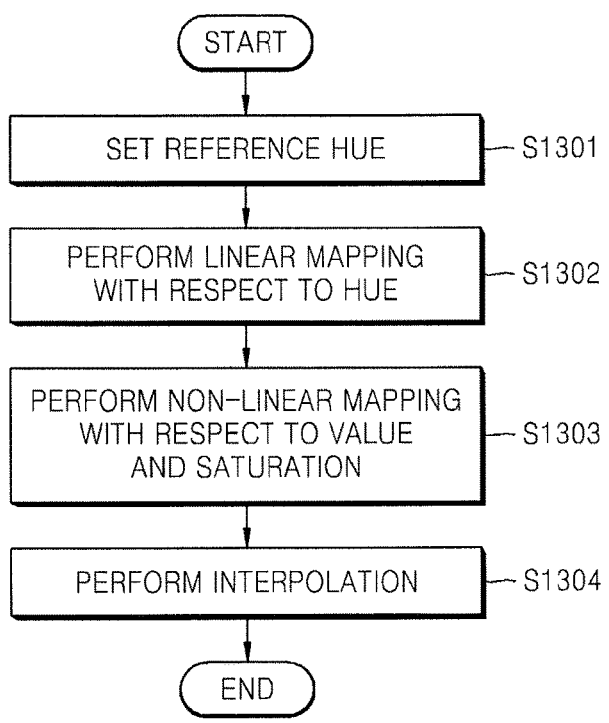

FIG. 13 is a flowchart illustrating a method of generating a color space map according to the exemplary embodiment.

Referring to FIG. 13, a reference hue is set in operation S1301, and a linear mapping is performed with respect to the reference hue in operation S1302. At this time, the reference hue is set as a complementary color of background color of an optical coherence tomographic image. In operation S1303, a non-linear mapping is performed with respect to value and saturation. At this time, a mapping value is set to clearly show an interest region of the optical coherence tomographic image. Finally, an interpolation is performed on a color space map in operation S1304 in order to reduce speckle noise.

Figure 14:
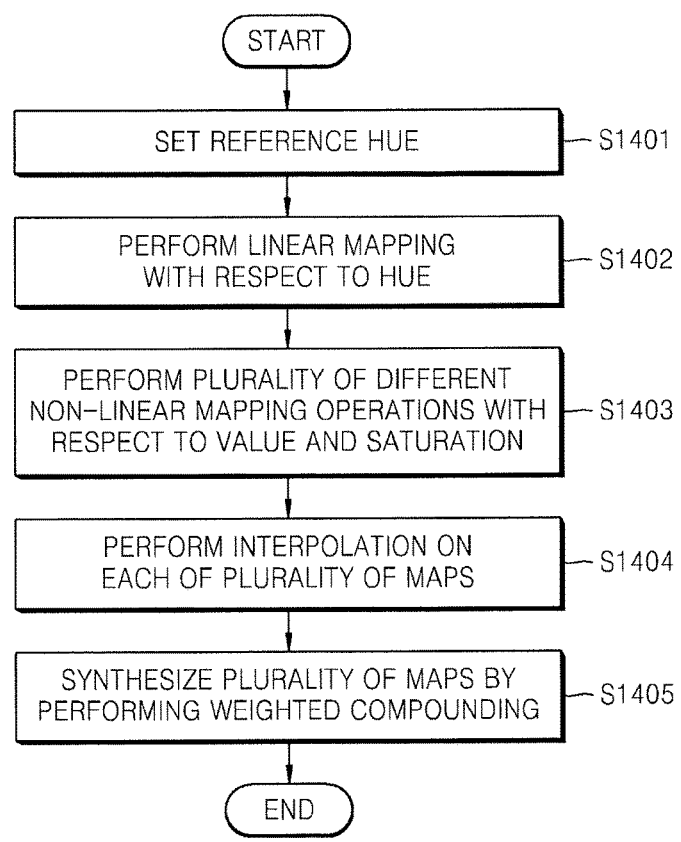

FIG. 14 is a flowchart illustrating a method of generating a color space map according to another exemplary embodiment.

Among operations of FIG. 14, operations S1401, S1402 and S1404 correspond to operations S1301, S1302 and S1304 of FIG. 13, respectively, and thus a detailed description thereof will not be repeated, and only operations S1403 and S1405 will be described. In operation S1403, a plurality of different color space maps on which different non-linear mapping operations are performed with respect to value and saturation are generated. At this time, each of the generated plurality of different color space maps improves contrast of different regions. Accordingly, a color space map having an improved discrimination may be obtained by synthesizing the plurality of color space maps. To this end, in operation S1405, a weighted compounding is performed to synthesize a plurality of color space maps.

Figure 15:
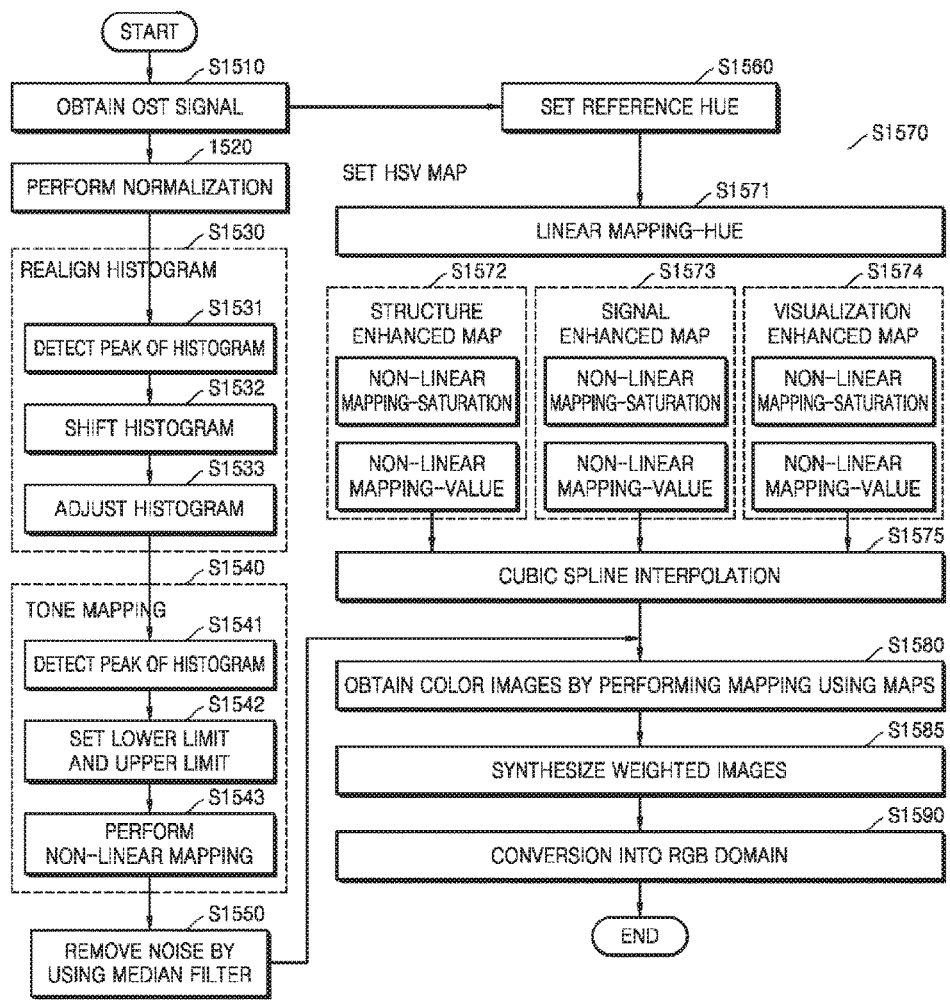

FIG. 15 is a detailed flowchart illustrating operations of a method of processing an optical coherence tomographic image according to an exemplary embodiment.

Referring to FIG. 15, in operation S1510, an OCT signal (i.e., an optical coherence tomographic image signal) is obtained. Normalization is performed in operation S1520, and a realignment of a histogram of an image is performed in operation S1530. In detail, operation S1530 may include an operation of detecting a peak of the histogram (operation S1531), an operation of shifting the histogram (operation S1532), and an operation of adjusting the histogram (operation S1533). For example, the histogram is shifted so that a peak point of the histogram corresponds to a central value of gray level intensity values.

In operation S1540, tone mapping is performed in order to improve contrast of an image. In detail, operation S1540 may include an operation of detecting a peak point of the histogram (operation S1541), an operation of setting a lower limit and an upper limit of the gray level intensity to set a region (operation S1542), and an operation of performing non-linear mapping for enlarging data within the region (operation S1543).

In operation S1550, noise may be removed using a median filter.

Meanwhile, when an OCT signal is obtained in operation S1510, a reference hue is set in operation S1560. The reference hue may be set as a complementary color of background color of the OCT image. An HSV map is generated in operation S1570. For example, a linear mapping is performed for hue in operation S1571, and non-linear mapping is performed with respect to saturation and value in operations S1572, S1573 and S1574, and thus three different HSV maps are generated. At this time, the generated three HSV maps have different effects such as structure enhanced map, signal enhanced map, and visualization enhanced map. In operation S1575, a cubic spline interpolation may be performed on each of the three HSV maps to reduce speckle noise.

When the three different HSV maps are generated, mapping is performed on the image data that is output in operation S1550 by using the three HSV maps, and three color images are obtained. Subsequently, a weighted compounding is performed on the three color images to generate one color image in operation S1585, and the color image are converted into an RGB domain in operation S1590, and thus a pseudo color image is output.

While not restricted thereto, an exemplary embodiment can be written as computer programs and can be implemented in general-use digital computers that execute the programs using a non-transitory computer readable medium which stores a program including the step of obtaining an optical coherence tomographic image by irradiating light to an object, the step of generating a color space map based on the obtained optical coherence tomographic image, the step of normalizing data of the obtained optical coherence tomographic image, the steps of realigning the normalized data of the optical coherence tomographic image, the step of performing tone mapping on the realigned data of the optical coherence tomographic image, and the step of generating a color image by mapping the data of the optical coherence tomographic image on which the tone mapping is performed, by using the generated color space map.

Examples of the non-transitory computer readable recording medium include magnetic storage media (e.g., ROM, RAM, magnetic tape, floppy disks, hard disks, etc.) and optical recording media (e.g., CD-ROMs, or DVDs). Also, the exemplary embodiments may be written as computer programs transmitted over a computer-readable transmission medium, such as a carrier wave, and received and implemented in general-use digital computers that execute the programs.

As described above, mapping is performed on an optical coherence tomographic image by using a color space map to convert the optical coherence tomographic image into a pseudo color image, thereby improving discrimination of the image.

The foregoing exemplary embodiments and advantages are merely exemplary and are not to be construed as limiting. The present teaching can be readily applied to other types of apparatuses. Also, the description of the exemplary embodiments of the present inventive concept is intended to be illustrative, and not to limit the scope of the claims, and many alternatives, modifications, and variations will be apparent to those skilled in the art.

What is claimed is:

1. A method of processing an optical coherence tomographic image, the method y comprising:
    obtaining an optical coherence tomographic image by irradiating light to an object;
    generating a color space map based on the obtained optical coherence tomographic image;
    normalizing data of the obtained optical coherence tomographic image;
    realigning the normalized data of the optical coherence tomographic image;
    performing tone mapping on the realigned data of the optical coherence tomographic image; and
    generating a color image by mapping the data of the optical coherence tomographic image on which the tone mapping is performed, by using the generated color space map,
    wherein properties of the color space map comprise a hue having a linear characteristic, while a brightness and a saturation have a non-linear characteristic, and
    wherein mapping values of hue corresponding to gray level intensity values are set to have a constant gradient.

2. The method of claim 1,
    wherein the generating the color space map comprises generating a plurality of color space maps, and
    wherein the generating the color image comprises generating a plurality of color images by mapping the data of the optical coherence tomographic image on which the tone mapping is performed, by using the plurality of color space maps, and generating one color image by performing a weighted compounding on the generated plurality of color images.

3. The method of claim 1, wherein the generating the color space map comprises setting a reference hue, and setting the mapping values of hue corresponding to the gray level intensity values based on the reference hue.

4. The method of claim 3, wherein a complementary color of background hue with respect to a region indicating the object in the optical coherence tomographic image is set as the reference hue.

5. The method of claim 3, wherein the mapping values of hue are set to have a linear characteristic within a predetermined range from the mapping value of the reference hue.

6. The method of claim 3, wherein the generating the color space map further comprises:
    determining mapping values of brightness and saturation corresponding to two or more gray level intensity values to have a non-linear characteristic; and
    performing an interpolation on the determined mapping values.

7. The method of claim 1, wherein the normalizing the data comprises adjusting data such that gray level intensity of pixels of the optical coherence tomographic image have a value of equal to or greater than 0 and equal to or less than 1 or a value of equal to or greater than 0 and equal to or less than 255 in a case of 8 bits.

8. The method of claim 1, wherein the realigning the data comprises shifting the normalized data of the obtained optical coherence tomographic image such that gray level intensity having the highest frequency in the optical coherence tomographic image has a central value of all gray level intensity.

9. The method of claim 1, wherein the generating the color space map comprises generating a map with respect to any one color space among a hue saturation value (HSV), a hue saturation intensity (HIS), a lightness saturation hue (LCH), and a hue saturation brightness (HSB).

10. The method of claim 1, wherein the performing the tone mapping comprises setting an upper limit and a lower limit of a region, and performing a non-linear process such as enlargement or reduction on image data within the region.

11. A non-transitory computer readable recording medium having embodied thereon a computer program for executing the method of claim 1.

12. An apparatus for processing an optical coherence tomographic image, the apparatus comprising:
    an image receiver configured to receive an optical coherence tomographic image;
    a color space map generator configured to generate a color space map based on the received optical coherence tomographic image;
    a normalization performer configured to normalize data of the received optical coherence tomographic image;
    a shifting performer configured to realign the normalized data of the optical coherence tomographic image;
    a tone mapping performer configured to perform a tone mapping on the realigned data of the optical coherence tomographic image; and
    a color space mapping performer configured to generate a color image by mapping the data of the optical coherence tomographic image on which the tone mapping is performed, by using the generated color space map,
    wherein properties of the color space map comprise a hue having a linear characteristic, while a brightness and a saturation have a non-linear characteristic, and
    wherein mapping values of the hue corresponding to gray level intensity values are set to have a constant gradient.

13. The apparatus of claim 12,
    wherein the color space map generator generates a plurality of color space maps, and
    wherein the color space mapping performer generates a plurality of color images by mapping the data of the optical coherence tomographic image on which the tone mapping is performed, by using the plurality of color space maps, and generates one color image by performing a weighted compounding on the generated plurality of color images.

14. The apparatus of claim 12, wherein the color space map generator sets a reference hue, and sets the mapping values of hue corresponding to the gray level intensity values based on the reference hue.

15. The apparatus of claim 14, wherein the color space map generator sets a complementary color of background hue with respect to a region indicating an object in the optical coherence tomographic image as the reference hue.

16. The apparatus of claim 14, wherein the color space map generator determines mapping values of brightness and saturation corresponding to two or more gray level intensity values to have a non-linear characteristic, and performs an interpolation on the determined mapping values.

17. The apparatus of claim 12, wherein the shifting performer shifts the normalized data of the obtained optical coherence tomographic image such that gray level intensity having the highest frequency in the optical coherence tomographic image has a central value of all gray level intensity.

18. The apparatus of claim 12, wherein the tone mapping performer sets an upper limit and a lower limit of a region, and performs a non-linear process such as enlargement or reduction on image data within the region.

* * * * *